(12) United States Patent
Janssen et al.

(10) Patent No.: US 9,283,188 B2
(45) Date of Patent: *Mar. 15, 2016

(54) DELIVERY SYSTEMS FOR DELIVERING FUNCTIONAL COMPOUNDS TO SUBSTRATES AND PROCESSES OF USING THE SAME

(75) Inventors: Robert Allen Janssen, Alpharetta, GA (US); Earl C. McCraw, Jr., Duluth, GA (US); Kimberlee Fay Thompson, Atlanta, GA (US); John Gavin MacDonald, Decatur, GA (US); Thomas David Ehlert, Neenah, WI (US); Patrick Sean McNichols, Hortonville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1035 days.

This patent is subject to a terminal disclaimer.

(21) Appl. No.: 11/530,210

(22) Filed: Sep. 8, 2006

(65) Prior Publication Data

US 2008/0063718 A1     Mar. 13, 2008

(51) Int. Cl.
| | |
|---|---|
| A61K 9/14 | (2006.01) |
| B01J 19/10 | (2006.01) |
| A61K 8/25 | (2006.01) |
| A61K 8/26 | (2006.01) |
| A61K 33/06 | (2006.01) |
| A61K 9/00 | (2006.01) |
| A61K 47/06 | (2006.01) |

(52) U.S. Cl.
CPC . *A61K 9/143* (2013.01); *A61K 8/25* (2013.01); *A61K 8/26* (2013.01); *A61K 33/06* (2013.01); *B01J 19/10* (2013.01); *A61K 9/0014* (2013.01); *A61K 47/06* (2013.01)

(58) Field of Classification Search
CPC ...... B01F 3/0819; B01F 3/1242; B01J 19/10; B01J 20/08; B01J 20/103; B01J 20/3441; B01J 2220/46; A61L 9/014
See application file for complete search history.

(56) References Cited

U.S. PATENT DOCUMENTS

| | | |
|---|---|---|
| 2,115,056 A | 4/1938 | Samuel |
| 2,307,206 A | 1/1943 | Fischer |
| 2,584,053 A | 1/1952 | Seavey et al. |
| 2,615,692 A | 10/1952 | Muller |
| 2,620,894 A | 12/1952 | Peterson et al. |
| 2,661,192 A | 12/1953 | Horsley et al. |
| 2,946,981 A | 7/1960 | O'Neill |
| 3,066,232 A | 11/1962 | Branson |
| 3,160,138 A | 12/1964 | Platzman |
| 3,202,281 A | 8/1965 | Weston |
| 3,239,998 A | 3/1966 | Carter et al. |
| 3,246,881 A | 4/1966 | Davidson et al. |
| 3,249,453 A | 5/1966 | Schnoring et al. |
| 3,273,631 A | 9/1966 | Neuman |
| 3,275,787 A | 9/1966 | Newberry |
| 3,278,165 A | 10/1966 | Gaffney |
| 3,284,991 A | 11/1966 | Ploeger et al. |
| 3,325,348 A | 6/1967 | Bennett |
| 3,326,470 A | 6/1967 | Loudin et al. |
| 3,338,992 A | 8/1967 | Kinney |
| 3,341,394 A | 9/1967 | Kinney |
| 3,425,951 A | 2/1969 | Ishiwata |
| 3,463,321 A | 8/1969 | VanIngen |
| 3,479,873 A | 11/1969 | Hermanns |
| 3,490,584 A | 1/1970 | Balamuth |
| 3,502,763 A | 3/1970 | Hartman |
| 3,519,251 A | 7/1970 | Nystrom et al. |
| 3,542,345 A | 11/1970 | Kuris |
| 3,542,615 A | 11/1970 | Dobo et al. |
| 3,567,185 A | 3/1971 | Ross et al. |
| 3,591,946 A | 7/1971 | Loe |
| 3,664,191 A | 5/1972 | Hermanns |
| 3,692,618 A | 9/1972 | Dorschner et al. |
| 3,782,547 A | 1/1974 | Dieter |
| 3,802,817 A | 4/1974 | Matsuki et al. |
| 3,865,350 A | 2/1975 | Burtis |
| 3,873,071 A | 3/1975 | Tatebe |
| 3,904,392 A | 9/1975 | VanIngen et al. |
| 4,035,151 A | 7/1977 | Czerny et al. |
| 4,062,768 A | 12/1977 | Elliot |
| 4,070,167 A | 1/1978 | Barbee et al. |
| 4,122,797 A | 10/1978 | Kawamura et al. |
| 4,168,295 A | 9/1979 | Sawyer |
| 4,218,221 A | 8/1980 | Cottell |

(Continued)

FOREIGN PATENT DOCUMENTS

| | | |
|---|---|---|
| CA | 2175065 | 5/1995 |
| CH | 657067 | 8/1986 |
| CN | 1535249 A | 10/2004 |
| CN | 1247628 | 3/2006 |
| CN | 101153138 | 4/2008 |
| DE | 2131878 A1 | 2/1973 |
| DE | 262553 A3 | 12/1988 |
| DE | 9017338 | 3/1991 |
| DE | 3922299 C1 | 4/1991 |
| DE | 4444525 | 6/1996 |

(Continued)

OTHER PUBLICATIONS

Kuo, Sheng-Lung, et al., Materials Chemistry and Physics, 86 (2004) 5-10.*

(Continued)

*Primary Examiner* — Sean Basquill
*Assistant Examiner* — Mark V Stevens (57) ABSTRACT

Delivery systems for incorporating functional compounds into substrates for use in various consumer products are disclosed. Specifically, the delivery system includes a carrier component comprising an ultrasonically energized adsorbent and one or more functional compounds. The ultrasonically energized adsorbent can adsorb the desired functional compounds and bind the functional compounds to the surface of the substrate.

15 Claims, 3 Drawing Sheets

(56) References Cited

U.S. PATENT DOCUMENTS

| | | | |
|---|---|---|---|
| 4,249,986 A * | 2/1981 | Obeda ................... | 156/580.1 |
| 4,259,021 A | 3/1981 | Goudy, Jr. | |
| 4,260,389 A | 4/1981 | Lister | |
| 4,266,879 A | 5/1981 | McFall | |
| 4,340,563 A | 7/1982 | Appel et al. | |
| 4,372,296 A | 2/1983 | Fahim | |
| 4,398,925 A | 8/1983 | Trinh et al. | |
| 4,425,718 A | 1/1984 | Kawaguchi | |
| 4,511,254 A | 4/1985 | North et al. | |
| 4,556,467 A | 12/1985 | Kuhn | |
| 4,612,016 A | 9/1986 | Jaeger et al. | |
| 4,612,018 A | 9/1986 | Tsuboi et al. | |
| 4,663,220 A | 5/1987 | Wisneski et al. | |
| 4,673,512 A | 6/1987 | Schram | |
| 4,693,879 A | 9/1987 | Yoshimura et al. | |
| 4,699,636 A | 10/1987 | Bofinger et al. | |
| 4,706,509 A | 11/1987 | Riebel | |
| 4,708,878 A | 11/1987 | Hagelauer et al. | |
| 4,726,522 A | 2/1988 | Kokubo et al. | |
| 4,743,361 A | 5/1988 | Schram | |
| 4,848,159 A | 7/1989 | Kennedy et al. | |
| 4,877,516 A | 10/1989 | Schram | |
| 4,879,011 A | 11/1989 | Schram | |
| 4,929,279 A | 5/1990 | Hays | |
| RE33,524 E | 1/1991 | Schram | |
| 4,983,045 A | 1/1991 | Taniguchi | |
| 5,006,266 A | 4/1991 | Schram | |
| 5,026,167 A | 6/1991 | Berliner, III | |
| 5,032,027 A | 7/1991 | Berliner, III | |
| 5,059,249 A | 10/1991 | Hays | |
| 5,096,532 A | 3/1992 | Neuwirth et al. | |
| 5,110,403 A | 5/1992 | Ehlert | |
| 5,122,165 A | 6/1992 | Wang et al. | |
| 5,164,094 A | 11/1992 | Stuckart | |
| 5,169,067 A | 12/1992 | Matsusaka et al. | |
| 5,242,557 A | 9/1993 | Jones et al. | |
| 5,258,413 A | 11/1993 | Isayev | |
| 5,260,243 A * | 11/1993 | Dunne et al. ................... | 502/68 |
| 5,269,297 A | 12/1993 | Weng et al. | |
| 5,326,164 A | 7/1994 | Logan | |
| 5,330,100 A | 7/1994 | Malinowski | |
| 5,335,449 A | 8/1994 | Beatty | |
| 5,372,634 A | 12/1994 | Monahan | |
| 5,373,212 A | 12/1994 | Beau | |
| 5,375,926 A | 12/1994 | Omasa | |
| 5,391,000 A | 2/1995 | Taniguchi | |
| 5,466,722 A | 11/1995 | Stoffer et al. | |
| 5,519,670 A | 5/1996 | Walter | |
| 5,536,921 A | 7/1996 | Herdrick et al. | |
| 5,583,292 A | 12/1996 | Karbach et al. | |
| 5,585,565 A | 12/1996 | Glascock et al. | |
| 5,665,383 A | 9/1997 | Grinstaff et al. | |
| 5,681,457 A | 10/1997 | Mahoney | |
| 5,711,888 A | 1/1998 | Trampler et al. | |
| 5,770,124 A * | 6/1998 | Marecki et al. ............ | 264/1.36 |
| 5,803,270 A | 9/1998 | Brodeur | |
| 5,810,037 A | 9/1998 | Sasaki et al. | |
| 5,831,166 A | 11/1998 | Kozuka et al. | |
| 5,853,456 A | 12/1998 | Bryan et al. | |
| 5,868,153 A | 2/1999 | Cohen et al. | |
| 5,873,968 A | 2/1999 | Pike et al. | |
| 5,902,489 A | 5/1999 | Yasuda et al. | |
| 5,916,203 A | 6/1999 | Brandon et al. | |
| 5,922,355 A | 7/1999 | Parikh et al. | |
| 5,935,883 A | 8/1999 | Pike | |
| 5,937,906 A | 8/1999 | Kozyuk | |
| 5,964,926 A | 10/1999 | Cohen | |
| 5,979,664 A | 11/1999 | Brodeur | |
| 6,010,592 A | 1/2000 | Jameson et al. | |
| 6,020,277 A | 2/2000 | Jameson | |
| 6,035,897 A | 3/2000 | Kozyuk | |
| 6,053,028 A | 4/2000 | Kraus, Jr. et al. | |
| 6,053,424 A | 4/2000 | Gipson et al. | |
| 6,055,859 A | 5/2000 | Kozuka et al. | |
| 6,060,416 A | 5/2000 | Kobata | |
| 6,074,466 A | 6/2000 | Iwasa | |
| 6,090,731 A | 7/2000 | Pike et al. | |
| 6,106,590 A | 8/2000 | Ueno et al. | |
| 6,169,045 B1 | 1/2001 | Pike et al. | |
| 6,200,486 B1 | 3/2001 | Chahine et al. | |
| 6,218,483 B1 | 4/2001 | Muthiah et al. | |
| 6,221,258 B1 | 4/2001 | Feke et al. | |
| 6,254,787 B1 | 7/2001 | Kimura et al. | |
| 6,266,836 B1 | 7/2001 | Gallego Juarez et al. | |
| 6,315,215 B1 | 11/2001 | Gipson et al. | |
| 6,322,240 B1 | 11/2001 | Omasa | |
| 6,332,541 B1 | 12/2001 | Coakley et al. | |
| 6,361,697 B1 | 3/2002 | Coury et al. | |
| 6,368,414 B1 | 4/2002 | Johnson | |
| 6,380,264 B1 | 4/2002 | Jameson et al. | |
| 6,383,301 B1 | 5/2002 | Bell et al. | |
| 6,450,417 B1 | 9/2002 | Gipson et al. | |
| 6,467,350 B1 | 10/2002 | Kaduchak et al. | |
| 6,482,327 B1 | 11/2002 | Mori et al. | |
| 6,506,584 B1 | 1/2003 | Chandler et al. | |
| 6,547,903 B1 | 4/2003 | McNichols et al. | |
| 6,547,935 B2 | 4/2003 | Scott | |
| 6,547,951 B1 | 4/2003 | Maekawa | |
| 6,551,607 B1 | 4/2003 | Minerath, III | |
| 6,576,042 B2 | 6/2003 | Kraus et al. | |
| 6,582,611 B1 | 6/2003 | Kerfoot | |
| 6,593,436 B2 | 7/2003 | Austin et al. | |
| 6,605,252 B2 | 8/2003 | Omasa | |
| 6,617,588 B1 | 9/2003 | Sato | |
| 6,620,226 B2 | 9/2003 | Hutton et al. | |
| 6,624,100 B1 | 9/2003 | Pike et al. | |
| 6,627,265 B2 | 9/2003 | Kutilek | |
| 6,655,826 B1 | 12/2003 | Leanos | |
| 6,659,365 B2 | 12/2003 | Gipson et al. | |
| 6,676,003 B2 | 1/2004 | Ehlert et al. | |
| 6,689,730 B2 | 2/2004 | Hortel et al. | |
| 6,739,524 B2 | 5/2004 | Taylor-McCune et al. | |
| 6,770,600 B1 | 8/2004 | Lamola | |
| 6,817,541 B2 | 11/2004 | Sands et al. | |
| 6,818,128 B2 | 11/2004 | Minter | |
| 6,837,445 B1 | 1/2005 | Tsai | |
| 6,841,921 B2 | 1/2005 | Stegelmann | |
| 6,858,181 B2 | 2/2005 | Aoyagi | |
| 6,878,288 B2 | 4/2005 | Scott | |
| 6,883,724 B2 | 4/2005 | Adiga et al. | |
| 6,890,593 B2 | 5/2005 | Tian | |
| 6,897,628 B2 | 5/2005 | Gunnerman | |
| 6,902,650 B2 | 6/2005 | Park et al. | |
| 6,911,153 B2 | 6/2005 | Minter | |
| 6,929,750 B2 | 8/2005 | Laurell et al. | |
| 6,935,770 B2 | 8/2005 | Schueler | |
| 6,936,151 B1 | 8/2005 | Lock | |
| 7,018,546 B2 | 3/2006 | Kurihara et al. | |
| 7,083,322 B2 | 8/2006 | Moore et al. | |
| 7,083,764 B2 | 8/2006 | Scott | |
| 7,090,391 B2 | 8/2006 | Taniguchi | |
| 7,108,137 B2 | 9/2006 | Lal et al. | |
| 7,150,779 B2 | 12/2006 | Meegan, Jr. | |
| 7,156,201 B2 | 1/2007 | Peshkovskiy et al. | |
| 7,293,909 B2 | 11/2007 | Taniguchi | |
| 7,322,431 B2 | 1/2008 | Ratcliff | |
| 7,338,551 B2 | 3/2008 | Kozyuk | |
| 7,404,666 B2 | 7/2008 | Tessien | |
| 7,414,009 B2 | 8/2008 | Tanaka et al. | |
| 7,419,519 B2 | 9/2008 | Li et al. | |
| 7,424,883 B2 | 9/2008 | McNichols et al. | |
| 7,465,426 B2 | 12/2008 | Kerherve et al. | |
| 7,504,075 B2 | 3/2009 | Marhasin | |
| 7,516,664 B2 | 4/2009 | Meier et al. | |
| 7,533,830 B1 | 5/2009 | Rose | |
| 7,582,156 B2 | 9/2009 | Tanaka et al. | |
| 7,673,516 B2 | 3/2010 | Janssen et al. | |
| 7,703,698 B2 | 4/2010 | Janssen et al. | |
| 7,712,353 B2 | 5/2010 | Janssen et al. | |
| 7,735,751 B2 | 6/2010 | Ehlert et al. | |
| 7,780,743 B2 | 8/2010 | Greaves et al. | |
| 7,785,674 B2 | 8/2010 | Janssen et al. | |
| 2001/0040935 A1 | 11/2001 | Case | |
| 2002/0036173 A1 | 3/2002 | Feke et al. | |

(56) References Cited

U.S. PATENT DOCUMENTS

| | | |
|---|---|---|
| 2002/0164274 A1 | 11/2002 | Haggett et al. |
| 2003/0042174 A1 | 3/2003 | Austin |
| 2003/0047067 A1 | 3/2003 | Kraus et al. |
| 2003/0048692 A1 | 3/2003 | Cohen et al. |
| 2003/0051989 A1 | 3/2003 | Austin |
| 2003/0061939 A1 | 4/2003 | Hutton et al. |
| 2003/0066899 A1 | 4/2003 | Gipson |
| 2003/0116014 A1 | 6/2003 | Possanza et al. |
| 2003/0143110 A1 | 7/2003 | Kritzler |
| 2003/0148042 A1* | 8/2003 | Wang ............................ 427/601 |
| 2003/0194692 A1 | 10/2003 | Purdum |
| 2003/0234173 A1 | 12/2003 | Minter |
| 2004/0022695 A1 | 2/2004 | Simon et al. |
| 2004/0065599 A1 | 4/2004 | Lal et al. |
| 2004/0079580 A1 | 4/2004 | Manna et al. |
| 2004/0120904 A1 | 6/2004 | Lye et al. |
| 2004/0142041 A1* | 7/2004 | MacDonald et al. ......... 424/489 |
| 2004/0187524 A1 | 9/2004 | Sen et al. |
| 2004/0202728 A1 | 10/2004 | Shanker et al. |
| 2005/0000914 A1 | 1/2005 | Dahlberg et al. |
| 2005/0008560 A1 | 1/2005 | Kataoka et al. |
| 2005/0017599 A1 | 1/2005 | Puskas |
| 2005/0025797 A1 | 2/2005 | Wang |
| 2005/0042129 A1 | 2/2005 | Kazem |
| 2005/0082234 A1 | 4/2005 | Solenthaler |
| 2005/0084438 A1 | 4/2005 | Do et al. |
| 2005/0084464 A1 | 4/2005 | McGrath et al. |
| 2005/0085144 A1* | 4/2005 | MacDonald et al. ........... 442/59 |
| 2005/0092931 A1 | 5/2005 | Gadgil et al. |
| 2005/0094486 A1 | 5/2005 | Taniguchi |
| 2005/0129161 A1 | 6/2005 | Laberge |
| 2005/0207431 A1 | 9/2005 | Beca et al. |
| 2005/0208303 A1 | 9/2005 | Atarashi et al. |
| 2005/0220665 A1 | 10/2005 | Ding |
| 2005/0260106 A1 | 11/2005 | Marhasin |
| 2006/0000034 A1 | 1/2006 | McGrath |
| 2006/0008442 A1 | 1/2006 | MacDonald et al. |
| 2006/0120212 A1 | 6/2006 | Taniguchi et al. |
| 2006/0207431 A1 | 9/2006 | Baca et al. |
| 2007/0062801 A1 | 3/2007 | Foret |
| 2007/0114306 A1 | 5/2007 | Kawakami et al. |
| 2007/0119785 A1 | 5/2007 | Englehardt et al. |
| 2007/0131034 A1 | 6/2007 | Ehlert et al. |
| 2007/0170277 A1* | 7/2007 | Ehlert et al. ................ 239/102.2 |
| 2008/0061000 A1 | 3/2008 | Janssen |
| 2008/0062811 A1 | 3/2008 | Janssen |
| 2008/0063718 A1 | 3/2008 | Janssen et al. |
| 2008/0067418 A1 | 3/2008 | Ross |
| 2008/0069887 A1 | 3/2008 | Baran et al. |
| 2008/0117711 A1 | 5/2008 | Omasa |
| 2008/0155763 A1 | 7/2008 | Janssen et al. |
| 2008/0156737 A1 | 7/2008 | Janssen et al. |
| 2008/0159063 A1 | 7/2008 | Janssen et al. |
| 2008/0192568 A1 | 8/2008 | Hielscher et al. |
| 2008/8251375 | 10/2008 | Hielscher et al. |
| 2009/0014377 A1 | 1/2009 | Janssen et al. |
| 2009/0147905 A1 | 6/2009 | Janssen et al. |
| 2009/0155091 A1 | 6/2009 | Ehlert et al. |
| 2009/0158936 A1 | 6/2009 | Janssen et al. |
| 2009/0162258 A1 | 6/2009 | Janssen et al. |
| 2009/0165654 A1 | 7/2009 | Koenig et al. |
| 2009/0166177 A1 | 7/2009 | Wenzel et al. |
| 2009/0168590 A1 | 7/2009 | Koenig et al. |
| 2009/0168591 A1 | 7/2009 | Wenzel et al. |
| 2009/0262597 A1 | 10/2009 | Kieffer et al. |
| 2010/0150859 A1 | 6/2010 | Do et al. |
| 2010/0206742 A1 | 8/2010 | Janssen et al. |
| 2010/0296975 A1 | 11/2010 | Peshkovsky et al. |
| 2013/0299737 A1* | 11/2013 | Park et al. ................. 252/182.32 |

FOREIGN PATENT DOCUMENTS

| | | |
|---|---|---|
| DE | 19618217 A1 | 11/1997 |
| DE | 19854013 | 5/2000 |
| DE | 19913397 A1 | 9/2000 |
| DE | 19938254 | 2/2001 |
| DE | 19938254 A1 | 2/2001 |
| DE | 10015144 A1 | 10/2001 |
| DE | 29825063 | 6/2004 |
| DE | 202005009923 U1 | 4/2005 |
| DE | 102004040233 | 3/2006 |
| DE | 102005025118 | 1/2007 |
| DE | 102005034629 | 1/2007 |
| EP | 0269941 A1 | 6/1988 |
| EP | 0292470 | 11/1988 |
| EP | 347891 | 12/1989 |
| EP | 0457187 A2 | 11/1991 |
| EP | 0459967 | 12/1991 |
| EP | 0625482 A | 11/1994 |
| EP | 0648531 | 4/1995 |
| EP | 0894612 A2 | 2/1999 |
| EP | 1375432 A1 | 2/2004 |
| EP | 1527812 A1 | 4/2005 |
| EP | 1954388 | 3/2007 |
| EP | 0983968 | 3/2008 |
| EP | 2173669 A2 | 4/2010 |
| EP | 2176173 A2 | 4/2010 |
| FR | 2793811 | 11/2000 |
| FR | 2832703 | 5/2003 |
| FR | 2832703 A1 | 5/2005 |
| GB | 1404575 | 9/1975 |
| JP | 56028221 | 3/1981 |
| JP | 57119853 | 7/1982 |
| JP | 58034051 | 2/1983 |
| JP | 62001413 A | 1/1987 |
| JP | 62039839 U | 3/1987 |
| JP | 6372364 | 4/1988 |
| JP | 63104664 | 5/1988 |
| JP | 1108081 | 4/1989 |
| JP | 2025602 | 1/1990 |
| JP | 02281185 A | 11/1990 |
| JP | 03053195 A | 3/1991 |
| JP | 3086258 | 4/1991 |
| JP | 03-157129 A | 5/1991 |
| JP | 6228824 | 8/1994 |
| JP | 8304388 | 11/1996 |
| JP | 9286943 | 11/1997 |
| JP | 10060331 | 3/1998 |
| JP | 11133661 | 5/1999 |
| JP | 2000158364 | 12/1999 |
| JP | 2000024494 A * | 1/2000 |
| JP | 2001017970 | 1/2001 |
| JP | 2001252588 | 9/2001 |
| JP | 2003103152 A | 4/2003 |
| JP | 2004020176 | 1/2004 |
| JP | 2004256783 | 9/2004 |
| JP | 2005118688 | 5/2005 |
| JP | 2007-144446 | 6/2007 |
| KR | 20020073778 A | 9/2002 |
| KR | 1020040069718 | 8/2004 |
| KR | 1020050013858 A | 2/2005 |
| KR | 1020050113356 A | 12/2005 |
| SU | 203582 A | 1/1967 |
| WO | 9400757 | 1/1994 |
| WO | 9420833 | 9/1994 |
| WO | 9429873 A | 12/1994 |
| WO | 9600318 | 1/1996 |
| WO | 9609112 A1 | 3/1996 |
| WO | 9620017 A1 | 7/1996 |
| WO | 9743026 | 11/1997 |
| WO | 9817373 | 4/1998 |
| WO | 9844058 | 10/1998 |
| WO | 99/33520 | 7/1999 |
| WO | 0004978 | 2/2000 |
| WO | 0041794 | 7/2000 |
| WO | 0139200 A | 5/2001 |
| WO | 0222252 | 3/2002 |
| WO | 0250511 | 6/2002 |
| WO | 0280668 A2 | 10/2002 |
| WO | 03012800 | 2/2003 |
| WO | 03102737 | 12/2003 |
| WO | 2004026452 | 4/2004 |
| WO | 2004064487 | 8/2004 |

(56) References Cited

FOREIGN PATENT DOCUMENTS

| | | |
|---|---|---|
| WO | 2005/011804 | 2/2005 |
| WO | 2005014489 A1 | 2/2005 |
| WO | 2006037591 | 4/2006 |
| WO | 2006043970 A2 | 4/2006 |
| WO | 2006073645 A1 | 7/2006 |
| WO | 2006074921 | 7/2006 |
| WO | 2006/093804 A | 9/2006 |
| WO | 2007011520 A2 | 1/2007 |
| WO | 2007060245 A1 | 5/2007 |
| WO | 2007095871 | 8/2007 |
| WO | 2008029311 A1 | 3/2008 |
| WO | 2008029379 | 3/2008 |
| WO | 2008047259 | 4/2008 |
| WO | 2008085806 | 7/2008 |
| WO | 2009007920 A2 | 1/2009 |
| WO | 2009083875 A2 | 7/2009 |

OTHER PUBLICATIONS

Sivakumar, M., Res. Chem. Intermed., vol. 30, No. 7-8, pp. 785-792 (2004).*
Maatar et al (Industrial Crops and Products, 2013, vol. 49, pp. 33-42).*
Zhang et al (Environmental Engineering Science, 2003, vol. 20, pp. 57-64).*
International Search Report and Written Opinion regarding PCT/IB2007/054892 dated May 15, 2008.
International Search Report and Written Opinion regarding PCT/IB2007/054898 dated May 15, 2008.
International Search Report and Written Opinion regarding PCT/IB2008/055395, dated Sep. 14, 2009.
International Search Report and Written Opinion for PCT/IB2008/052764 mailed Apr. 2, 2009.
Non-final office action regarding U.S. Appl. No. 11/617,515, dated Mar. 27, 2009.
International Search Report and Written Opinion regarding PCT/IB2008/052760, dated Feb. 17, 2009.
International Search Report and Written Opinion, PCT/IB2008/055051 (Feb. 20, 2009).
European Office Action regarding European Application No. 07805228.9, dated Oct. 9, 2009.
International Search Report and Written Opinion regarding PCT/IB2008/055394, dated Sep. 28, 2009.
Blume, T. and Neis, U. "Improved wastewater disinfection by ultrasonic pre-treatment." Ultrasonics Sonochemistry, 2004, No. 11, pp. 333-336.
International Search Report and Written Opinion issued Aug. 18, 2009 for PCT/IB2008/055520.
International Search Report and Written Opinion issued Aug. 18, 2009 for PCT/IB2008/055517.
International Search Report and Written Opinion issued Aug. 18, 2009 for PCT/IB2008/055518.
Final Office Action Regarding U.S. Appl. No. 11/530,311, dated Jun. 23, 2009.
Non-final office action regarding U.S. Appl. No. 11/950,943, dated May 1, 2009.
J.D. Lawson, "Some Criteria for a Power Producing Thermonuclear Reactor", Proc. Phys. Soc. B70, pp. 6-10 (1957).
L.A. Artsimovich, "Controlled Thermonuclear Reactions", Gordon and Breach Science Publishers, New York, first English translation, 1964.
D.R.O. Morrison, "Cold Fusion Update No. 9", Jan. 1994, from Newsgroups sci.physics.fusion, http://www.groups.google.com.
Brenner et al, Single-bubble sonoluminescence, Reviews of Modern Physics, vol. 74, Apr. 2002, pp. 425-484.
J. Lister, Plasma Physics and Controlled Fusion 48, pp. 715-716 (2006).
U.S. Department of Energy, "Report of the Review of Low Energy Nuclear Reactions", Dec. 1, 2004 (USDOE).
International Search Report and Written Opinion from PCT/IB2008/052766, dated Mar. 31, 2009.
Non-final Office action regarding U.S. Appl. No. 11/965,435, dated Mar. 11, 2010.
English translation of Nagel WO 2006/074921 Al, accessed on the EPO website.
Non-final Office Action regarding U.S. Appl. No. 12/335,231, dated Oct. 15, 2009.
Non-final office action regarding U.S. Appl. No. 11/617,497, dated Jun. 26, 2009.
International Search Report and Written Opinion regarding PCT/IB2007/052947, dated Mar. 3, 2008.
Non-final office action regarding U.S. Appl. No. 11/530,311, dated Nov. 5, 2008.
International Search Report and Written Opinion regarding PCT/IB2008/055396, dated Jul. 29, 2009.
U.S. Appl. No. 11/966,447, filed Dec. 28, 2007.
Peplow, Mark, "Desktop fusion is back on the table," viewed at http//nature.com/news/2006/060109/full/060109-5.html on May 4, 2007.
International Search Report and Written Opinion regarding PCT/IB2007/052988, dated Feb. 14, 2008.
Taleyarkhan, et al., "Evidence for Nuclear Emissions During Acoustic Cavitation," Science, (Mar. 8, 2002), vol. 295, pp. 1868-1873.
Kloeppel, James E. "Temperature inside collapsing bubble four times that of the sun," News Bureau, University of Illinois at Urbana-Champaign.
Tal-Figiel B., The Formation of Stable W/O, O/W, W/O/W Cosmetic Emulsions in an Ultrasonic Field, viewed at http://www.atypon-link.com/ICHEME/doi/abs/10.1205/cherd06199 on Oct. 19, 2007.
"Controlled Thermonuclear Fusion" viewed at http://library.thinkquest.org/17940/texts/fusion_controlled/fusion_controlled.html on Oct. 23, 2007.
Flannigan, "Measurement of Pressure and Density Inside a Single Sonoluminescing Bubble," Physical Review Letters (May 26, 2006), PRL 96.
Taleyarkhan, et al. "Additional Evidence of Nuclear Emissions During Acoustic Cavitation," Physical Review E, (Mar. 2004). vol. 69.
"Thermonuclear Fusion Energy Source for Future Generations," viewed at http://nature.com/news/2006/060109/full/060109-5.html on May 4, 2007.
Lachey, Taleyarkhan, and Nigmatulin, "Bubble Power," IEEE spectrum, May 2005, pp. 39-43.
International Search Report and Written Opinion regarding PCT/IB2007/053621, dated Feb. 14, 2008.
International Search Report and Written Opinion regarding PCT/IB2007/053623, dated Feb. 14, 2008.
International Search Report and Written Opinion regarding PCT/IB2007/053622, dated Feb. 14, 2008.
U.S. Appl. No. 11/777,140, filed Jul. 12, 2007.
U.S. Appl. No. 11/617,497, filed Dec. 28, 2006.
U.S. Appl. No. 11/617,515, filed Dec. 28, 2006.
U.S. Appl. No. 11/777,151, filed Jul. 12, 2007.
U.S. Appl. No. 11/950,943, filed Dec. 5, 2007.
U.S. Appl. No. 11/963,139, filed Dec. 21, 2007.
U.S. Appl. No. 11/963,237, filed Dec. 21, 2007.
U.S. Appl. No. 11/966,458, filed Dec. 28, 2007.
U.S. Appl. No. 11/966,472, filed Dec. 28, 2007.
U.S. Appl. No. 11/966,418, filed Dec. 28, 2007.
U.S. Appl. No. 11/777,145, filed Dec. 12, 2007.
U.S. Appl. No. 11/965,435, filed Dec. 27, 2007.
International Search Report and Written Opinion regarding PCT/IB2008/055514, dated Aug. 25, 2009.
International Search Report and Written Opinion regarding PCT/IB2007/052945, dated Feb. 1, 2008.
Non-final Office action regarding U.S. Appl. No. 11/530,183, dated Apr. 19, 2010.
Takehi Moriguchi, et al. "Metal-modified silica adsorbents for removal of humic substances in water." Journal of Colloid and Interface Science 283, 2005 300-310, See Abstract, pp. 301 and 304.
International Search Report and Written Opinion regarding PCT/IB2009/055090, dated Jul. 16, 2010.

(56) References Cited

OTHER PUBLICATIONS

International Search Report and Written Opinion regarding PCT/IB2009/055092, dated Jul. 16, 2010.
Non-final Office action regarding U.S. Appl. No. 11/963,237, dated Jul. 8, 2010.
Non-final Office action issued in related application U.S. Appl. No. 11/777,140 on Aug. 9, 2010.
Non-Final Office action issued in related application U.S. Appl. No. 11/966,418 on Aug. 2, 2010.
Non-Final Office action issued in related application U.S. Appl. No. 11/966,447 on Aug. 2, 2010.
Oct. 27, 2010 Letter regarding the Office action issued for Mexican Patent Application Serial No. MX/a/2009/002519 mailed Oct. 12, 2010.
Supplementary European Search Report issued in EP Application No. 08789242 mailed Dec. 17, 2010.
Barbaglia et al., "Search of Fusion Reactions During the Cavitation of a Single Bubble in Deuterated Liquids," Physica Scripta 72, pp. 75-78 (2005).
Extended European Search Report for EP Patent Application No. 08867871.9, mailed Sep. 27, 2012.
First Office Action for China Patent Application No. 200880121407.2, dated Aug. 24, 2011.
EP Office Action for Patent Application No. 08 789 246.9-2104 dated Sep. 4, 2012; 4 pages.
First Office Action for China Patent Application No. 20088016947.3, dated Jun. 24, 2011.
First Office Action for Russian Patent Application No. 2009112526, dated Apr. 28, 2011.
Non-Final Office Action issued for U.S. Appl. No. 11/963,139, mailed Jun. 15, 2011.
Non-Final Office Action issued for U.S. Appl. No. 12/335,231, mailed Jul. 13, 2011.
Non-Final Office Action issued for U.S. Appl. No. 12/335,176, mailed Jul. 13, 2011.
Sivakumar, et al., Preparation of Nanosized TiO2 Supported on Activated Alumina by a Sonochemical Method: observation of an increased photocatalytic decolourisation efficiency, Res. Chem. Intermed., vol. 30, No. 7-8, pp. 785-792 (2004).
Chinese First Office Action for Patent Application No. 200880123174.X dated Sep. 20, 2012; 8 pages.
Compton R G et al., "Electrode Processes at the Surfaces of Sonotrodes," Electrochimica ACTA, vol. 41, No. 2, pp. 315-320 (Feb. 1, 1996).
Extended European Search Report received in EP Patent Application No. 08789246.9 mailed Nov. 30, 2011.
Chinese Office Action for Patent Application No. 200880123174.X dated Mar. 27, 2013; 5 pages.
EP Office Action for Patent Application No. 08 789 248.5-2104 dated Sep. 4, 2012; 4 pages.
Non-final Office Action received in U.S. Pat. No. 12/438,317, mailed Sep. 24, 2012.
Extended European Search Report received in EP Patent Application No. 08789248.5 dated Nov. 30, 2011.
Chinese First Office Action for Patent Application No. 200880123172.0 dated Oct. 10, 2012; 9 pages.
Extended European Search Report received in EP Patent Application No. 08868425 dated Feb. 14, 2012.
First Office Action for Chinese Patent Application No. 200880123165.0 dated Oct. 10, 2012; 9 pages.
First Office Action for China Patent Application No. 200780033331.3, dated Nov. 14, 2011.
European Search Report regarding European Application No. 08789248.5, dated May 2, 2013; 3 pages.
Non-final Office action issued for U.S. Appl. No. 12/335,176 (Jun. 6, 2013).
Extended European Search Report regarding European Application No. 13159386.5, dated May 3, 2013; 8 pages.
European Extended Search Report received in EP Application No. 08868778.5, dated Jul. 22, 2013.
Extended European Search Report regarding European Application No. 08867345.4, dated Jul. 24, 2013; 8 pages.
European Extended Search Report received in EP Application No. 08868912.0, dated Jan. 2, 2014.
European Communication received in EP Application No. 08868778.5, dated Oct. 22, 2014.

\* cited by examiner

DELIVERY SYSTEMS FOR DELIVERING FUNCTIONAL COMPOUNDS TO SUBSTRATES AND PROCESSES OF USING THE SAME

BACKGROUND OF DISCLOSURE

The present disclosure generally relates to delivery systems capable of delivering functional compounds to substrates for use in products. More particularly, the present disclosure relates to incorporating pharmaceutical and nutritional compounds into substrates using a delivery system with a carrier component comprising an ultrasonically energized adsorbent. The ultrasonically energized adsorbent can adsorb the desired functional compounds and bind the functional compounds to the surface of the substrate.

Many consumer products on today's market include functional compounds to improve the product's characteristics. The functional compounds can be any material that acts upon a substrate or otherwise provides a benefit once delivered to the desired location. Examples of functional compounds that may enhance the value of a product include pharmaceuticals that are intended to be ingested, transferred transdermally, or subcutaneously injected into a human or animal patient's body, vitamins and nutrients, and various other additives that can be similarly introduced into or onto the body of a patient.

Additionally, non-pharmaceutical functional compounds can be incorporated into consumer products to improve the product's overall value. For example, products whose use is mainly for outdoors, such as deck furniture and automobile covers, could benefit by having UV absorbing compounds (UV absorbers) incorporated onto their surfaces. By absorbing UV rays, these compounds could provide an outdoor product having improved aesthetic properties and durability.

While the desire to incorporate these types of functional compounds is known, the present methods for delivering the functional compounds to products are expensive and complex. Specifically, the present methods require the use of complex chemical formulations and long, complex chemical processes to incorporate the compounds into a delivery system to facilitate the delivery of the compounds into or onto a product.

Based on the foregoing, there is a need in the art for a delivery system that can inexpensively and efficiently deliver functional compounds to various consumer products. Additionally, it would be advantageous if the delivery system was capable of affixing to the functional compounds, but capable of readily releasing the compounds upon the occurrence of a selected event or trigger.

SUMMARY OF THE DISCLOSURE

The present disclosure is directed to delivery systems capable of delivering functional compounds into or onto substrates for use in consumer products. Generally, the delivery systems include a carrier component comprising an ultrasonically energized adsorbent and a functional compound. In one embodiment, the functional compound is a pharmaceutical or nutritional compound for use in a medicament to be used in or on a human or animal patient's body. In another embodiment, the functional compound is a UV absorber for use in an outdoor product such as deck furniture.

As such, the present disclosure is directed to a process of delivering functional compounds to a substrate. The process comprising: energizing an adsorbent with ultrasonic energy; adsorbing at least one functional compound to the surface of the energized adsorbent to form a carrier component of a delivery system; and contacting the carrier component with a substrate.

The present disclosure is further directed to a delivery system for delivering functional compounds to substrates. The delivery system comprising a carrier compound comprising an ultrasonically energized adsorbent and at least one functional compound.

Other features of the present disclosure will be in part apparent and in part pointed out hereinafter.

DETAILED DESCRIPTION OF THE PREFERRED EMBODIMENT

The present disclosure is generally directed to a delivery system for functional compounds and processes for using the same. Functional compounds, as noted above, are any material that acts upon a substrate or otherwise provides a benefit once delivered to the desired location. In one embodiment, the functional compounds can be any pharmaceutical and/or nutritionally suitable substance that can provide a benefit to a location on or within a patient's body once delivered. As used herein, the term "patient" refers to both human and non-human patients. In another embodiment, the functional compounds can be used to provide a benefit to an inanimate substrate or product.

In accordance with the present disclosure, the delivery system is generally directed to the construction of a carrier component containing an energized adsorbent and one or more functional compounds and use of such a carrier component to selectively deliver the functional compounds contained on the component to a substrate. More particularly, the carrier component acts as a carrier for a functional compound.

Specifically, the energized adsorbent contained within the carrier component provides a bonding site on the surface of the component for a functional compound. The functional compounds become adsorbed onto the surface of the energized adsorbent. Once the functional compound is bonded to the energized adsorbent, the resulting carrier component can then be used to deliver the functional compound to a particular location. The carrier component can be used as is, for instance, or can be combined with a liquid, gel, or other vehicle which may facilitate delivery of the component depending upon the particular application. Such liquid and gel vehicles are known to those skilled in the art. The carrier component and/or vehicle can also be used in conjunction with a drug delivery apparatus, such as a bandage or modified tampon.

Various different adsorbents can be used in the present disclosure. In one particularly preferred embodiment, the adsorbent is alumina. Specifically, alumina powder alone or alumina-containing beads/particles may be used, depending upon the functional compound and the trigger for releasing it. In one embodiment, the alumina is an alumina powder, preferably a Brockmann I activated aluminum oxide powder (also referred to herein as activated alumina).

Activated alumina is manufactured by mild calcinations of aluminum hydroxide (aluminum trihydrate, boehmite), which is an intermediate in the industrial production of aluminum from Bauxite. Specifically, it is precipitated from a sodium aluminate solution. By heating the aluminum hydroxide so obtained at temperatures around 500° C., approximately 33% (by weight) constitutional water is removed, and the crystal structure of the boehmite remains intact.

Aluminas are hydrophilic and have high capacities. As such, activated alumina could suitable capture anionic dyes and surfactants, and chelate with many non-polar dyes. For example, dyes with $SO_3$—, $CO_2$—, and $PO_3$— substituents can suitably bind to the surface of activated alumina. Additionally, structures having polyhydroxy groups such as 1,2-dihydroxybenzene can suitably chelate with activated alumina. Examples of polyhydroxy containing structures can include, for example:

A full range of standardized aluminas are available with defined activities, pH values, and particles sizes. Activated alumina can be characterized by its Brockmann activity (e.g., activity grades of I, II, III, IV, and V), which is measured using the Brockmann and Schodder test disclosed in Brockmann & Schodder, Ber. Dtsh. Chem. Ges., 74B, 73 (1941). Generally, the activity grade is measured as follows: a standardized volume of a pair of test dyes dissolved in a standard solvent is applied to a standardized column, and after chromatographic development, the activity grade is shown by whether the test dyes separate or not. The test dye pairs that can be used are: (I) azobenzene and p-methoxyazobenzene, (Ii) p-methoxyazobenzene and Sudan Yellow, (III) Sudan Yellow and Sudan Red, (IV) Sudan Red and p-aminoazobenzene, and (V) p-aminoazobenzene and p-hydroxyazobenzene. Specifically, 20 milligrams of each of the two dyes from the above dye pairs is weighed into 50 milliliters of a solvent mixture containing one part pure benzene and four parts pure petroleum ether (boiling point 50-70° C.) to produce test dye solutions. Ten milliliters of each test dye solution are then applied to the top of a column containing 100-150 millimeters of the adsorbent to be tested. The columns are then eluted with 20 milliliters of eluent, which is the same mixture as used for the solvent above. To determine the activity grade, the migration distance of the test dye in front is measured. The activity grade is then given by the number of the pair of test dyes, in addition to the distance, in millimeters, from the top of the column to the front of the foremost migrated dye. An activated alumina having a Brockmann I Activity is the most reactive.

Brockmann I activated alumina can be converted to grades of lower activity by simply adding water. Specifically, to convert a Brockmann I activated alumina to a Brockmann II activated alumina, 3% (by total weight activated alumina powder) water is added to the Brockmann I activated alumina. To convert the grade I activated alumina to a grade III activated alumina, 6% (by total weight activated alumina powder) water is added, for grade IV, 10% (by total weight activated alumina powder) water is added to the Brockmann I activated alumina, and for grade V, 15% (by total weight activated alumina powder) water is added.

Examples of suitable Brockmann I activated alumina powders are commercially available from CAMAG Scientific Inc. (Wilmington, N.C.) and Sigma-Aldrich (St. Louis, Mo.).

In another embodiment, the alumina can be a particle such as an alumina or silica bead or particle. The types of particles to be used depend on the functional compound and the trigger for releasing it. For example, in one particular embodiment, the alumina particles are activated alumina particles produced from the activated alumina powder described above.

Another suitable alumina particle is an alumina particle that can contain various other ingredients. In general, the particle can contain any material that does not adversely interfere with the ability of the functional compound to bond to alumina. In this regard, at least a portion of the alumina contained by the particle should be present on the surface of the particle so that the alumina is available for adsorbing the functional compound.

For example, in one embodiment, the alumina particles for use in delivering the functional compounds are alumina sol particles. Alumina sols are colloidal hydrous alumina that can maintain a wide range of viscosities and are highly heat resistant. Many different types of alumina sols are commercially available with varying particle sizes. Of particular advantage, alumina sols can be prepared that carry a relatively strong positive surface charge or zeta potential. In this embodiment, the particle that is reacted with the functional compound contains primarily, and in some embodiments, exclusively alumina. Examples of alumina particle materials include Aluminasol-100 and Aluminasol-200, which are both commercially available from Nissan Chemical America (Houston, Tex.).

In another embodiment, the particle can contain a core material coated with alumina. The alumina can form a continuous or a discontinuous coating over the particle. The core material can be, for instance, an inorganic oxide, such as silica. For example, in one embodiment, silica sols can be used that contain silica nanoparticles that have an alumina surface coating. Such sols are commercially available from Nissan Chemical America (Houston, Tex.). The silica is coated with alumina to provide stability to the sols over certain pH ranges. In fact, alumina coated silica sols may have greater stability in some applications of the present disclosure in comparison to pure alumina sols. Specific examples of alumina coated particles with silica cores include SNOWTEX-AK®, available from Nissan Chemical America (Houston, Tex.) and Ludox Cl®, available from Grace Davison (Columbia, Md.).

When the alumina is in particle form, the particles have an average particle size of from about 5 nanometers to less than 500 microns. More suitably, the alumina particles have an average particle size of from about 10 nanometers to less than 1 micron, and even more suitably, from about 15 nanometers to about 25 nanometers.

Other adsorbent materials are also suitable for use in the present disclosure. Examples include activated carbon and zeolites. Activated carbon is hydrophobic in nature and generally favors organic materials.

Generally, zeolites are hydrated alumino-silicate minerals with porous structures. They are hydrophilic with polar, regular channels, and are typically used in air separation and dehydration.

It has now been discovered that using an energized adsorbent provides for improved adsorption of the functional compounds onto the surface of the adsorbent. Generally, it has been found that an adsorbent that has been energized using ultrasonic energy can more efficiently and more effectively bind to functional compounds, allowing for an improved delivery of these functional compounds to substrates. Specifically, by subjecting the adsorbent in the ultrasonic treatment system to ultrasonic energy, microcavitation within the fluid containing the functional compounds will occur. As the small bubbles produced through microcavitation collapse or oscillate, microconvective currents are produced, which result in a flow of fluid in an otherwise stagnant zone. Additionally, the acoustic wave produced by the ultrasonic energy produces a pulsed bulk motion that further provides for fluid agitation. The increased fluid flow produced by both the microcavitation and the acoustic wave results in reducing the thickness of the hydrodynamic boundary layer that surrounds the adsorbent. This effect allows for improved mass transport of the functional compounds in the fluid to the surface of the adsorbent, allowing for a quicker, more effective adsorption.

The adsorbent can be energized with ultrasonic energy using any means known in the art. For example, in one embodiment, the ultrasonic energy is produced by an ultrasonic waveguide assembly including a horn assembly. In one form, the horn assembly comprises an elongate, generally cylindrical horn member. In general, the horn member may be constructed of a metal having suitable acoustical and mechanical properties. Suitable metals include aluminum, monel, titanium, and some alloy steels. In one preferred embodiment, the metal can be titanium-based material, such as commercially pure titanium, or a titanium alloy (e.g., $Ti_6Al_4V$).

The waveguide assembly also suitably comprises a booster coaxially aligned with and connected at an upper end thereof to the lower end of the horn assembly. It is understood, however, that the waveguide assembly may comprise only the horn assembly and remain within the scope of this disclosure.

A suitable ultrasonic drive system including at least an exciter and a power source is connected to the booster (and more broadly to the waveguide assembly) to energize the waveguide assembly to mechanically vibrate ultrasonically. Examples of suitable ultrasonic drive systems include a Model 20A3000 system available from Dukane Ultrasonics of St. Charles, Ill., and a Model 2000CS system available from Hermann Ultrasonics of Schaumberg, Ill.

In one embodiment, the drive system is capable of operating the waveguide assembly at a frequency in the range of from about 15 kHz to about 100 kHz, more suitably in the range of from about 15 kHz to about 60 kHz, even more suitably in the range of from about 20 kHz to about 40 kHz, and even more suitably at a frequency of about 35 kHz. Such ultrasonic drive systems are well known to those skilled in the art and need not be further described herein.

In addition to the energized adsorbent, the carrier component of the delivery system of the present disclosure includes one or more functional compounds. The functional compounds for use in the present disclosure can include any suitable pharmaceutical, nutritional, or other functional compound containing at least one of the following moieties: $SO_3-$, $CO_2-$, $PO_3-$, a tautomer thereof, or a functional equivalent thereof, wherein R and R' independently comprise a hydrogen, an alkyl group, or an aryl group. As used herein, a "functional equivalent" to one of the above moieties refers to functional compounds that include similar reactive groups as shown above, but which are not positioned on the molecule exactly as shown above and yet will bond with the energized adsorbent in a similar manner. Furthermore, it should be understood that various additional R groups may be included with the above moieties as long as the R groups do not interfere with the bond that is formed with the energized adsorbent.

The above moieties may form a relatively strong bond to the energized adsorbent surface. Without wishing to be bound by theory, it is believed that the above moieties form a bidentate ligand bonding system with the adsorbent's surfaces. Specifically, it is believed that the adsorbent forms a covalent bond and a coordinate bond with the above moieties. Furthermore, it is believed that a surface reaction occurs causing the functional compound to remain on the surface of the energized adsorbent (unless triggerably released) and form a coating thereon. The functional compound can cover the entire resulting adsorbent-containing carrier component or can be located at particular locations on the carrier component. Further, it should be understood that the components of the present disclosure can contain more than one functional compound so as to deliver multiple treatments to a substrate.

Generally, the functional compounds include pharmaceuticals, xenobiotics, therapeutic agents, nutritional agents, anti-viral agents, anti-microbial agents, UV absorbers, and signal agents. "Xenobiotics" is a general term used to describe any chemical interacting with an organism that does not occur in the normal metabolic pathways of that organism.

One suitable example of a therapeutic compound that may be used in the present delivery system is hydrocortisone. Hydrocortisone is a natural anti-inflammatory hormone of the glucocorticoid family of hormones produced by the adrenal cortex. Hydrocortisone has the structural formula:

Another suitable pharmaceutical that can be used as the therapeutic compound of the delivery system is an anti-microbial. One particularly preferred anti-microbial is tetracycline, which is an antibiotic substance produced by *Streptomyces* spp. Tetracycline has the structural formula:

Another preferred anti-microbial is an antifungal. Examples of antifungal compounds include salicylanilide and albofungin, which have the structural formulas:

Salicylanilide

Albofungin

In yet another embodiment, antiviral compounds can be used as the functional compounds in the delivery system of the present disclosure. For example, in one particular embodiment, the antiviral compound is an anthraquinone dye. Anthraquinone dyes include, for example, Acid Green 25 (also referred to as Alizarine Cyanine Green F), Alizarin Red S, Quinalizarin, and Hypericin. The structural formulas for these anthraquinone dyes are shown below:

Acid Green 25

Alizarin Red S

-continued

Quinalizarin

Hypericin

Other suitable pharmaceuticals can include Baicalin Hydrate, Baicalein, and Daunorubicin, which have been used as anticancer drugs by blocking proliferation and increasing apoptosis in human umbilical vascular endothelial cells. The formulas for these pharmaceuticals are shown below:

Baicalin Hydrate

Baicalein

Daunorubicin

Still additional pharmaceutical compounds which may be used in the delivery system of the present disclosure include salicylamide, salacetamide, and salsalate, which are analgesic, antipyretic, and anti-inflammatory compounds. The structural formulas for these compounds are provided below:

In addition to pharmaceutical compounds, nutritional compounds can be used as the functional compounds in the delivery system. Examples of nutritional compounds for use in the delivery system can include ascorbic acid (Vitamin C) and aspartame (phenylalanine). Ascorbic acid and aspartame have the structural formulas:

In another embodiment, the delivery system delivers ultraviolet (UV) absorbers to a substrate. UV absorbers are commonly used in products to slow down the product breakdown caused by exposure to sunlight. For example, UV absorbers can be used in products such as automobile covers, boat covers, deck furniture, and the like. UV absorbers are also useful in sunscreens and sunblocks. For example, suitable UV absorbers can include hydroxybenzophenones, which act as UV blockers by adsorbing the radiation and emitting the energy by an alternative pathway. Particularly preferred hydroxybenzophenones are 2,2'-dihydroxybenzophenone and 2,2',4,4'-tetrahydroxybenzophenone, whose chemical structures are shown below:

Other suitable UV absorbers include radical inhibitors. These compounds terminate polymer free radicals and stop the further breakdown of the polymer chains.

Of particular advantage, in many embodiments, it has also been discovered that a functional compound can be bonded to the energized adsorbent without significantly impacting the positive surface charge of the energized adsorbent, which can be measured as zeta potential. The term "zeta potential" as used herein means a potential gradient that arises across an interface. This term particularly refers to the potential gradient that arises across the interface between the Stern layer in contact with the carrier component of the delivery system of the present disclosure and the diffuse layer surrounding the component. Zeta potential measurements can be taken using, for example, a Zetapals instrument which is commercially available from the Brookhaven Instrument Corporation (Holtsville, N.Y.). In general, zeta potential measurements can be conducted by adding one to three drops of a sample into a cuvet containing 1 mM KCl solution, and using the instrument's default functions preset for aqueous solutions.

Thus, once the energized adsorbent is bonded to the functional material, the resulting carrier component continues to maintain a relatively strong positive charge. For example, carrier components made according to the processes set forth below can have a zeta potential of greater than 20 mV, suitably greater than 30 mV, and even more suitably, greater than 40 mV. By remaining positively charged, the components are well suited for being affixed to substrates that carry a negative surface charge through coulombic attraction. Depending upon the type of carrier component produced and the surface of the substrate, the bond of the carrier component in some embodiments can be relatively permanent and substantive. Consequently, the delivery system of the present disclosure can be used to affix functional compounds to various substrates without the use of chemical binders or other attachment structures. As an example, the carrier component of the delivery system can include along its surface a pharmaceutical functional compound, and yet the carrier component may still retain sufficient positive charge to allow it to be attached to a negatively charged bandage or other topically contacting substrate. Then upon the occurrence of a specific chemical or environmental stimulus, the functional compound contained on the carrier component can be selectively released to the body of a patient, and the carrier components will remain affixed to the bandage.

In a further embodiment, a signal agent, such as a fragrance or perfume, may be used by itself or in conjunction with one of the other functional compounds described above in the carrier component of the delivery system to both treat a substrate, and also to provide an indication to the consumer of the effectiveness of such treatment or the occurrence of a particular event. By way of example, a fragrance may be adsorbed to one bonding site of the energized adsorbent and an antibiotic may be adsorbed to a second bonding site of the energized adsorbent to form the carrier component of the delivery system. The delivery system can then be delivered to an infected site. Upon removal of the infection, and the return to a more normal acidic environment, the fragrance may be released, thereby providing an indication of the effective treatment of the infection.

One particularly preferred fragrance is the alkaline fragrance, salicyladehyde, which has the formula:

Salicylaldehyde

Other suitable signal agents can include dyes such as carminic acid and the like.

In a further example, the signal can be used to generate an indication of a particular event, such as the release of body fluids or exudates as in a bandage or a personal care product, such as a feminine care product or child care diaper product. For example, carminic acid on energized alumina would be released and change color when exposed to cadaverine, putrescine, or ammonia, which are indications of wound infection.

The carrier components used in the delivery system of the present disclosure can be present in various forms, shapes, and sizes depending upon the desired result. For example, the carrier components can be a sphere, a crystal, a rod, a disk, a tube, or a string of particles. The size of the carrier component can also vary dramatically. For instance, in one embodiment, the carrier component can have an average dimension of less than 1 millimeter. More suitably, the carrier component can have an average dimension of less than 500 microns, and even more suitably, of less than 100 microns. As used herein, the average dimension of the carrier component refers to the average length, width, height, or diameter of the carrier component.

As noted above, the present disclosure is also directed to processes of using the delivery system. Generally, the process for using the delivery system to deliver functional compounds to a substrate comprises: (1) energizing an adsorbent with ultrasonic energy; (2) adsorbing at least one functional compound to the surface of the energized adsorbent to form a carrier component for a delivery system; and (3) contacting the carrier component in the delivery system with a substrate.

To begin the process, an adsorbent is energized using ultrasonic energy. Specifically, in one suitable embodiment, an alumina powder or alumina-containing particle as described above is contacted with ultrasonic energy produced by the ultrasonic waveguide assembly as described above.

The energized adsorbent is then contacted with one or more functional compounds to adsorb the functional compound to the surface of the energized adsorbent. In one embodiment, the adsorption of the functional compound to the adsorbent takes place in a batch process. When adsorbing using a batch process, one or more functional compounds are dissolved in an aqueous solution with stirring at a rate of from about 5 revolutions per minute (rpm) to about 800 rpm in a storage tank. Suitably, the aqueous solution contains from about 0.1% (by weight) to about 50% (by weight) functional compounds with the balance being water. The aqueous solution typically has a temperature of from about 20° C. to about 90° C. and a pH of from about 2.0 to about 10. An ultrasonic horn, such as described above, is placed into this tank to activate the adsorbent. Adsorbent is then slowly added and activated with ultrasonic energy produced by the ultrasonic horn operating at a frequency of from about 15 kHz to about 100 kHz, more suitably at a frequency of from about 15 kHz to about 60 kHz, and even more suitably, from about 20 kHz to about 40 kHz. The mixture is stirred for about 10 seconds to about 10 minutes, suitably from about 5 minutes to about 10 minutes, to allow the functional compounds to bind to the surface of the energized adsorbent.

In another embodiment, the energizing of the adsorbent and the adsorption of the functional compound to the adsorbent takes place in a continuous ultrasonic treatment system.

Figure 1:
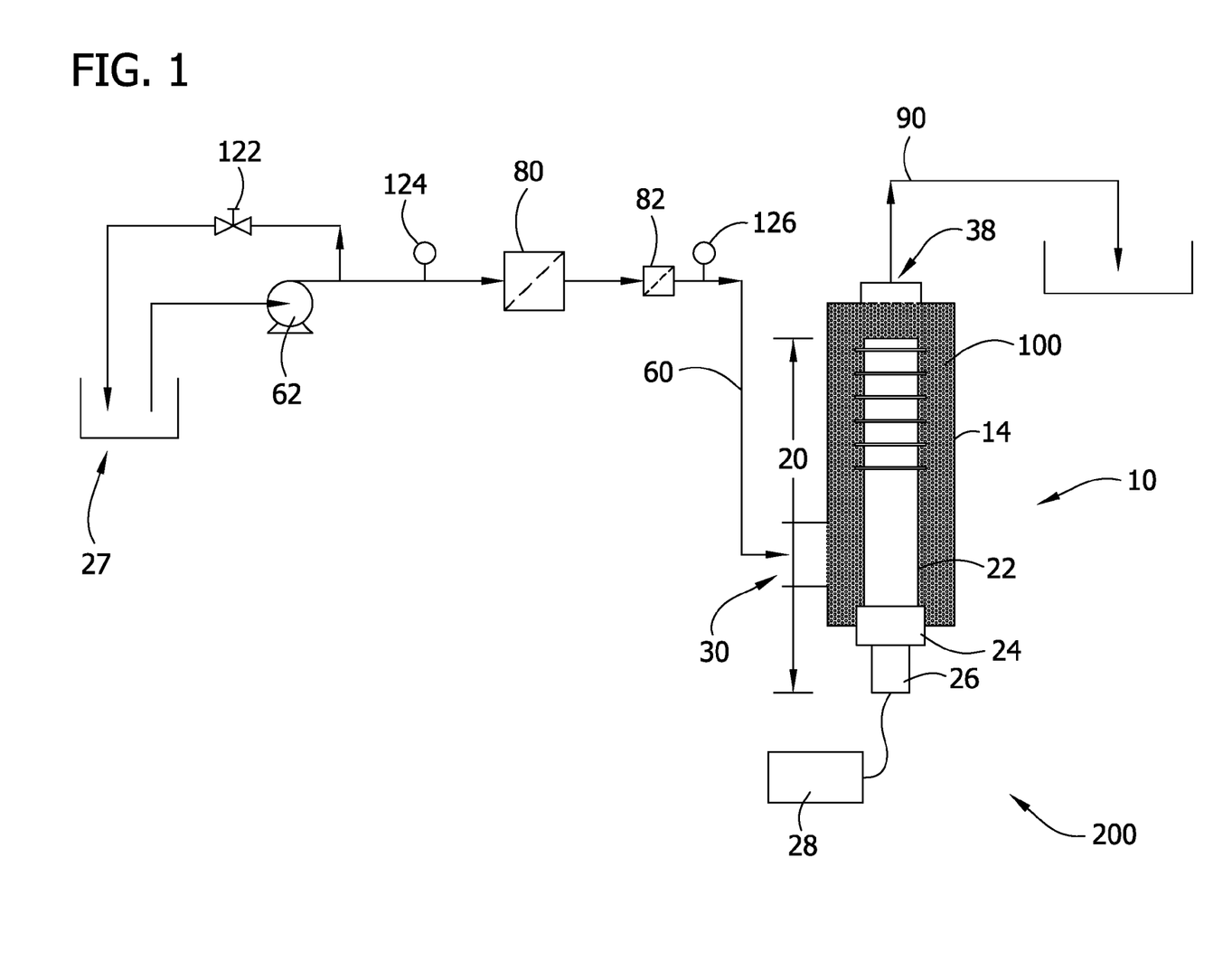
FIG. 1 is a schematic of one embodiment of an ultrasonic treatment system for ultrasonically energizing an adsorbent.

FIG. 1 provides an ultrasonic treatment system, generally indicated at 200, to energize adsorbents in accordance with one embodiment of the present disclosure. Generally, the ultrasonic treatment system 200 comprises an ultrasonic treatment chamber 10. As illustrated in FIG. 1, the ultrasonic treatment chamber 10 is generally elongate and is oriented vertically (e.g., a longitudinal axis of the chamber extends vertically) to define an inlet end 30 (a lower end in the orientation of the illustrated embodiment) and an outlet end 38 (an upper end in the orientation of the illustrated embodiment). The system 200 is configured such that fluid (e.g., aqueous solution containing functional compounds to be adsorbed to an adsorbent and added to a substrate) enters the treatment chamber 10 generally at the inlet end 30 thereof, flows generally longitudinally within the chamber 10 (e.g., upward in the orientation of the illustrated embodiment) and exits the chamber 10 generally at the outlet end 38 of the chamber 10.

The terms "upper" and "lower" are used herein in accordance with the vertical orientation of the ultrasonic treatment chamber illustrated in the various drawings and are not intended to describe the necessary orientation of the chamber in use. That is, while the chamber is most suitably oriented vertically, with the outlet end of the chamber above the inlet end as illustrated in the various drawings, it is understood that the chamber may be oriented with the inlet end above the outlet end, or it may be oriented other than in a vertical orientation and remain within the scope of this disclosure. The terms "axial" and "longitudinal" refer directionally herein to the lengthwise direction of the chamber (e.g., end-to-end such as the vertical direction in the illustrated embodiments). The terms "transverse," "lateral," and "radial" refer herein to a direction normal to the axial (e.g., longitudinal) direction. The terms "inner" and "outer" are also used in the reference to a direction transverse to the axial direction of the ultrasonic treatment chamber, with the term "inner" referring to a direction toward the interior of the chamber (e.g., toward the longitudinal axis of the chamber) and the term "outer" referring to a direction toward the exterior of the chamber (e.g., away from the longitudinal axis of the chamber).

The inlet end 30 may be produced using any suitable material, such as metal or plastic, and may be shaped in a variety of shapes. The inlet end 30 of the ultrasonic treatment chamber 10 is in fluid communication with a suitable storage stir tank, generally indicated at 27, that is operable to direct fluid 60 to, and more suitably through, the chamber 10.

Figure 2:
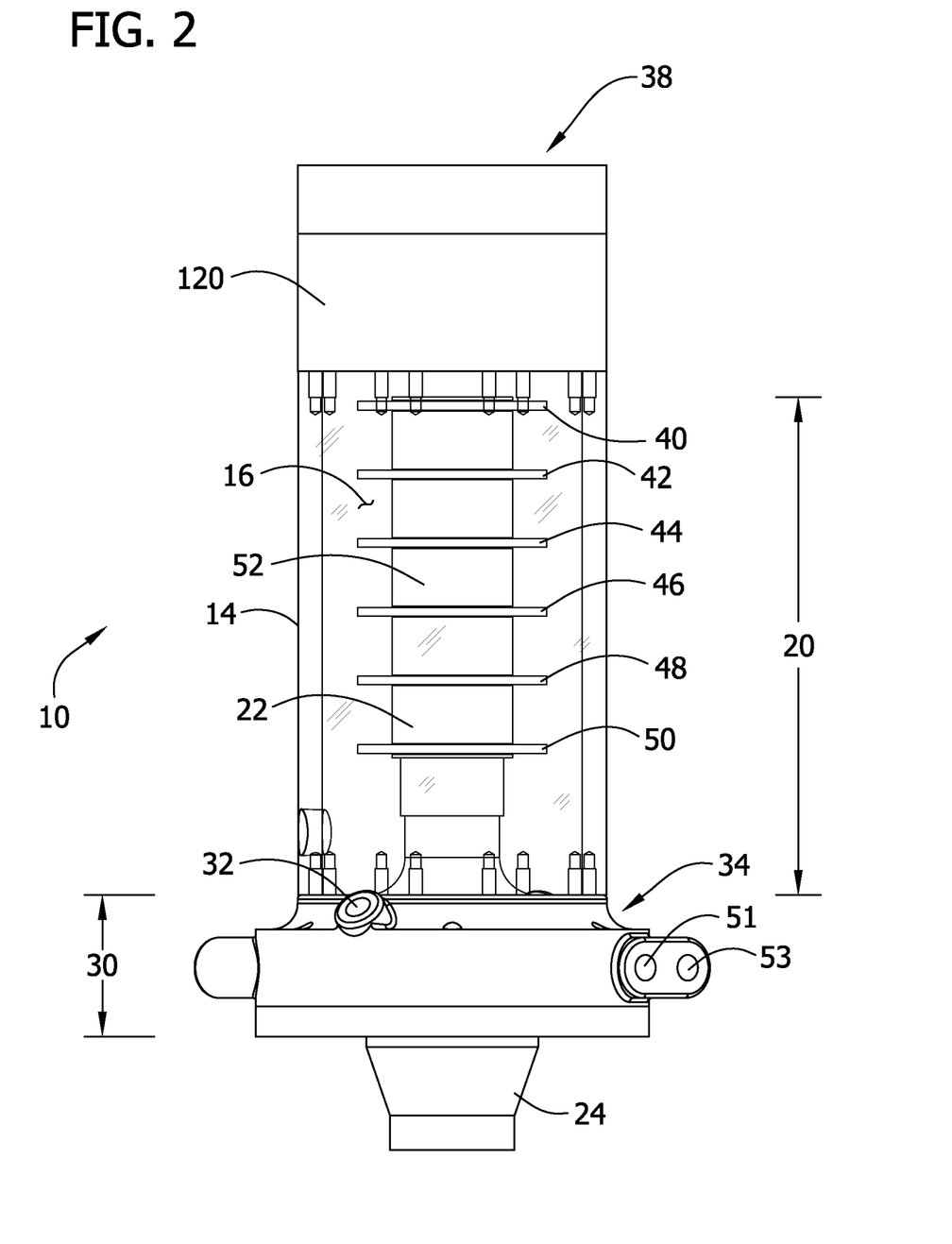
FIG. 2 is a side view of an ultrasonic treatment chamber comprising an ultrasonic waveguide assembly.

With reference now to FIG. 2, the ultrasonic treatment chamber 10 comprises an elongate, generally tubular column 14 having longitudinally opposite ends defining an interior space of the chamber 10 through which fluid delivered to the chamber 10 flows from the inlet end 30 to the outlet end 38 thereof. The column 14 is typically of a length that the functional compounds in the aqueous solution and adsorbent have sufficient residence time so that substantially complete adsorption of the functional compounds to the surface of the adsorbent is effectuated. For example, in one embodiment, the column 14 is suitably from about 6 to about 10 inches in length. More suitably, the column 14 is about 8.6 inches in length.

The column 14 general defines, at least in part, a sidewall of the chamber 10. As illustrated in FIG. 2, the column 14 has an inlet port 32 formed therein through which the fluid to be treated within the chamber 10 is delivered to the interior space 16 thereof. In the illustrated embodiment, the column 14 further comprises an inlet collar 34 that is connected to and mounted on one end of the sidewall to generally define the inlet end 30 of the chamber 10. The sidewall (e.g., defined by the elongate tubular column) of the chamber 10 has an inner surface that together with the collar 34 and outlet end 38 define the interior space 16 of the chamber 10. In the illustrated embodiment, the sidewall 14 is suitably generally annular in cross-section. However, it is contemplated that the cross-section of the chamber sidewall 14 may be other than annular, such as polygonal or another suitable shape, and remains within the scope of this disclosure. The chamber sidewall 14 of the illustrated chamber 10 is suitably constructed of a transparent material, although it is understood that any suitable material may be used as long as the material is compatible with the adsorbent to be energized, the pressure at which the chamber is intended to operate, and other environmental conditions such as temperature.

With particular reference to FIG. 2, the collar 34 defining the inlet end 30 of the chamber 10 is generally annular and has at least one, and more suitably a plurality of inlet ports (e.g., shown as 32, 51, and 53 in FIG. 2) formed therein for receiving fluid into the interior space 16 of the chamber 10. At least one inlet port is oriented generally tangentially relative to the annular collar 34 so that fluid flows into the interior space 16 of the chamber 10 generally tangentially thereto to impart a swirling action to the fluid as it enters the chamber 10. More suitably, in the illustrated embodiment, a pair of inlet ports 51 and 53 is arranged in parallel alignment with each other and extends generally tangentially relative to the annular collar, with one port being designated herein as the inner inlet port 51 and the other port being designated the outer inlet port 53.

The ultrasonic waveguide assembly such as described above and indicated in FIG. 2 at 20 extends longitudinally within the interior space 16 of the chamber 10 to ultrasonically energize the adsorbent, generally depicted at 100, located within the interior space 16 of the chamber 10 as described below. In particular, the waveguide assembly 20 of the illustrated embodiment extends longitudinally from the lower or inlet end 30 of the chamber 10 up into the interior space 16 thereof to a terminal end of the waveguide assembly. More suitably, the waveguide assembly 20 is connected, either directly or indirectly, to the chamber column 14 as will be described later herein.

The ultrasonic waveguide assembly 20 suitably comprises an elongate horn assembly such as described above and generally indicated at 22, disposed entirely within the interior space 16 of the column, e.g., for complete submersion within the fluid being treated within the chamber 10, and more suitably it is disposed coaxially with the chamber sidewall 14.

The horn assembly 22 has an outer surface that together with the inner surface of the sidewall 14 defines the flow path within the interior space 16 of the chamber 10 along which fluid and the functional compounds to be adsorbed flow past the horn assembly 22 within the chamber 10 (this portion of the flow path being broadly referred to herein as the ultrasonic treatment zone). The horn assembly 22 has an upper end defining a terminal end of the horn assembly 22 (and therefore the terminal end of the waveguide assembly) and a longitudinally opposite lower end. The waveguide assembly 20 of the illustrated embodiment also comprises a booster 24 coaxially aligned with and connected at an upper end thereof to the lower end of the horn assembly 22. It is understood, however, that the waveguide assembly 20 may comprise only the horn assembly 22 and remain within the scope of this disclosure. It is also contemplated that the booster 24 may be disposed entirely exterior of the chamber column 14, with the horn assembly 22 connected directly to the chamber column 14 without departing from the scope of this disclosure.

Figure 3:
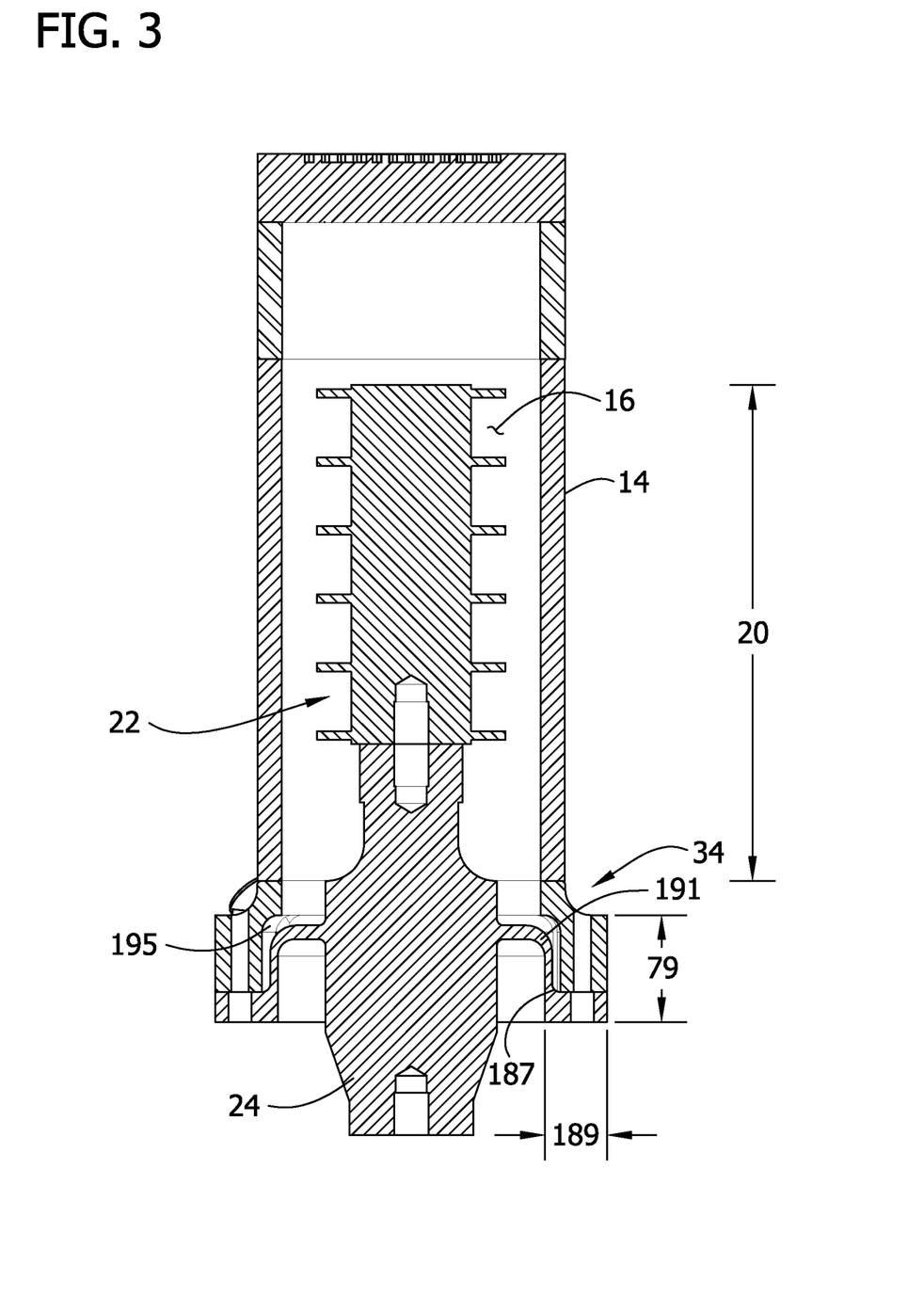
FIG. 3 is a longitudinal (e.g., vertical) cross-section of the chamber of FIG. 2.

As further illustrated in FIG. 3, the waveguide assembly 20, and more particularly the booster 24, is suitably connected to the chamber column 14, e.g., to the tubular column defining the chamber sidewall, at the upper end thereof by a mounting member 79 that is configured to vibrationally isolate the waveguide assembly 20 from the ultrasonic treatment chamber column 14. That is, the mounting member 79 inhibits the transfer of longitudinal and transverse (e.g., radial) mechanical vibration of the waveguide assembly 20 to the chamber column 14 while maintaining the desired transverse position of the axis of the waveguide assembly 20 (and in particular the horn assembly 22) within the interior space 16 of the chamber column 14 and allowing both longitudinal and radial displacement of the horn assembly 22 within the chamber column 14.

As one example, the mounting member 79 of the illustrated embodiment generally comprises an annular outer segment 189 extending transverse to the waveguide assembly 20 in transversely spaced relationship therewith, and a flange member 191 interconnecting the outer segment 189 to the wave guide assembly 20. While the flange member 191 and transverse outer segment 189 of the mounting member 79 extend continuously about the circumference of the waveguide assembly 20, it is understood that one or more of these elements may be discontinuous about the waveguide assembly 20 such as in the manner of wheel spokes, without departing from the scope of this disclosure. The outer segment 189 of the mounting member 79 is particularly configured to seat down against a shoulder formed by the inlet collar 34.

As seen best in FIG. 3, the internal cross-sectional dimension (e.g., internal diameter) of the collar 34 is stepped outward as the collar 34 extends longitudinally downward away from the chamber sidewall 14 to accommodate the flange member 191. In one particularly suitable embodiment, the collar 34 is sufficiently sized to be transversely spaced from the flange member 191 to define a generally annular gap 195 therebetween in which liquid delivered to the chamber 10 via the inlet ports of the collar 34 enters the interior space 16 of the chamber 10. This annular gap 195 further facilitates the swirling action of the effluent upon entry into the chamber via the collar inlet ports.

The mounting member 79 is suitably sized in transverse cross-section so that at least an outer edge margin of the outer segment 189, and more suitably a substantial transverse portion of the outer segment is seated on the shoulder formed on the collar 34. A suitable fastening system, such as a bolt and nut (not shown) arrangement secures the outer segment 189 of the mounting member 79 to the shoulder formed by the collar 34 to thereby connect the booster 24 (and more broadly to connect the waveguide assembly 20) to the chamber column 14.

The flange member 191 may suitably be constructed relatively thinner than the outer segment 189 of the mounting member 79 to facilitate flexing and/or bending of the flange member 191 in response to ultrasonic vibration of the waveguide assembly 20. As an example, in one embodiment the thickness of the flange member 191 may be in the range of about 0.2 mm to about 5 mm, and more suitably about 2.5 mm. The flange member 191 of the illustrated mounting member 79 suitably has an inner transverse component connected to the waveguide assembly 20 and extending generally transversely outward therefrom but inward of the outer segment 189 of the mounting member 79, and an axial, or longitudinal component interconnecting the transverse inner component with the outer segment 189 of the mounting member 79 and together with the transverse inner component generally forming a generally L-shaped cross-section of the flange member 191. It is contemplated, however, that the flange member may instead have a generally U-shaped cross-section or other suitable cross-sectional shape such as an H-shape, an I-shape, an inverted U-shape and the like and remain within the scope of this disclosure. Additional examples of suitable mounting member configurations are illustrated and described in U.S. Pat. No. 6,676,003, the entire disclosure of which is incorporated herein by reference to the extent it is consistent herewith.

The longitudinal component of the illustrated flange member 191 is suitably cantilevered to the transverse outer segment 189 and to the transverse inner component of the flange, while the inner component of the flange is cantilevered to the waveguide assembly 20. Accordingly, the flange member 191 is capable of dynamically bending and/or flexing relative to the outer segment 189 of the mounting member 79 in response to transverse vibratory displacement of the inner segment 187 of the mounting member 189 to thereby isolate the chamber column 14 from transverse and radial displacement of the waveguide assembly 20.

While in the illustrated embodiment the transverse outer segment 189 of the mounting member 79 and the transverse inner component of the flange member 191 are disposed generally at longitudinally offset locations relative to each other, it is understood that they may be disposed at generally the same location (e.g., where the flange member is generally U-shaped in cross-section) or at locations other than those illustrated in FIG. 3) without departing from the scope of this disclosure.

In one particularly suitable embodiment the mounting member 79 is of single piece construction. Even more suitably the mounting member 79 may be formed integrally with the booster 24 (and more broadly with the waveguide assembly) as illustrated in FIG. 3. However, it is understood that the mounting member 79 may be constructed separate from the waveguide assembly 20 and remain within the scope of this disclosure. It is also understood that one or more components of the mounting member 79 may be separately constructed and suitably connected or otherwise assembled together.

In one suitable embodiment the mounting member 79 is further constructed to be generally rigid (e.g., resistant to static displacement under load) so as to hold the waveguide assembly 20 in proper alignment within the interior space 16 of the chamber 10. For example, the rigid mounting member in one embodiment may be constructed of a non-elastomeric material, more suitably metal, and even more suitably the same metal from which the booster (and more broadly the waveguide assembly) is constructed. The term rigid is not, however, intended to mean that the mounting member is incapable of dynamic flexing and/or bending in response to ultrasonic vibration of the waveguide. In other embodiments, the rigid mounting member may be constructed of an elastomeric material that is sufficiently resistant to static displacement under load but is otherwise capable of dynamic flexing and/or bending in response to ultrasonic vibration of the waveguide assembly. While the mounting member 79 illustrated in FIG. 3 is constructed of a metal, and more suitably constructed of the same material as the booster, it is contemplated that the mounting member may be constructed of other suitable generally rigid materials without departing from the scope of this disclosure.

A suitable ultrasonic drive system such as described above and including at least an exciter 26 and a power source 28 is disposed exterior of the chamber 10 and connected to the booster 24 (and more broadly to the waveguide assembly 20) to energize the waveguide assembly 20 to mechanically vibrate ultrasonically. Examples of suitable ultrasonic drive systems include a Model 20A3000 system available from Dukane Ultrasonics of St. Charles, Ill., and a Model 2000CS system available from Herrmann Ultrasonics of Schaumberg, Ill.

In one embodiment, the drive system is capable of operating the waveguide assembly at a frequency in the range of from about 15 kHz to about 100 kHz, more suitably in the range of from about 15 kHz to about 60 kHz, even more suitably in the range of from about 20 kHz to about 40 kHz, and even more suitably at a frequency of about 20 kHz. Such ultrasonic drive systems are well known to those skilled in the art and need not be further described herein.

With particular reference to FIG. 2, the horn assembly 22 comprises the elongate, generally cylindrical horn member having an outer surface, and two or more agitating members connected to the horn member and extending at least in part transversely outward from the outer surface of the horn member in longitudinally spaced relationship with each other. In the illustrated embodiment, the agitating members comprise a series of six washer-shaped rings 40, 42, 44, 46, 48, and 50 that encircle the horn member in longitudinally spaced relationship with each other and radially outward from the outer surface of the horn member. It is understood, however, that the agitating members need not each be continuous about the circumference of the horn member. For example, the agitating members may suitably instead take the form of spokes, fins or other discrete structural members that extend transversely outward from the outer surface of the horn member.

As one example of the relative spacing between the rings, the horn member suitably has a length of about 5.25 inches (133.4 mm). One of the rings is disposed adjacent the terminal end of the horn member (and hence of the waveguide assembly), and more suitably is longitudinally spaced approximately 0.063 inches (1.6 mm) from the terminal end of the horn member. The rings are each about 0.125 inches (3.2 mm) in width and are longitudinally spaced from each other (between facing surfaces of the rings) a distance of about 0.875 inches (22.2 mm).

It is understood that the number of agitating members (e.g., the rings in the illustrated embodiment) may be less than or more than six without departing from the scope of this disclosure. It is also understood that the longitudinal spacing between the agitating members may be other than as illustrated in FIG. 2 and described above (e.g., either closer or spaced further apart). While the rings illustrated in FIG. 2 are equally longitudinally spaced from each other, it is alternatively contemplated that where more than two agitating members are present the spacing between longitudinally consecutive agitating members need not be uniform to remain within the scope of this disclosure.

In particular, the locations of the agitating members are at least in part a function of the intended displacement of the agitating members upon vibration of the horn member. For example, in the illustrated embodiment the horn member has a nodal region 52 located generally longitudinally centrally of the horn member (e.g., between the third and fourth rings). As used herein, the "nodal region" of the horn member refers to a longitudinal region or segment of the horn member along which little (or no) longitudinal displacement occurs during ultrasonic vibration of the horn member and transverse (e.g., radial in the illustrated embodiment) displacement of the horn member is generally maximized. Transverse displacement of the horn member suitably comprises transverse expansion of the horn member but may also include transverse movement (e.g., bending) of the horn member.

In the illustrated embodiment, the configuration of the horn member is such that the nodal region 52 is particularly defined by a nodal plane (i.e., a plane transverse to the horn member at which no longitudinal displacement occurs while transverse displacement is generally maximized). This plane is also sometimes referred to as a nodal point.

Accordingly, agitating members 40 and 50 (e.g., in the illustrated embodiment, rings) that are disposed more distally from the nodal region of the horn member will experience primarily axial (e.g., longitudinal) displacement while agitating members 46 an 48 that are nearer to the nodal region 52 will experience an increased amount of transverse displacement and a decreased amount of axial displacement relative to the longitudinally most distal agitating members. It is understood that the horn member may be configured so that the nodal region is other than longitudinally centrally located on the horn member without departing from the scope of this disclosure.

Still referring to FIG. 2, the agitating members are sufficiently sized in thickness and transverse length (i.e., the distance that the agitating member extends transversely outward from the outer surface of the horn member) to facilitate dynamic flexing/bending of the agitating members in response to the ultrasonic vibration of the horn member. In one suitable embodiment, a ratio of the transverse length of the agitating member to the thickness of the agitating member is in the range of about 2:1 to about 6:1. As one example, the rings each extend transversely outward from the outer surface of the horn a length of about 0.5 inches (12.7 mm) and the thickness of each ring is about 0.125 inches (3.2 mm), so that the ratio of transverse length to thickness of each ring is about 4:1. It is understood, however that the thickness and/or the transverse length of the agitating members may be other than as described above without departing from the scope of this disclosure. Also, while the rings of the illustrated embodiment each have the same transverse length and thickness, it is understood that the agitating members may have different thicknesses and/or transverse lengths.

The transverse length of the agitating member also at least in part defines the size (and at least in part the direction) of the flow path along which effluent in the interior space 16 of the chamber column 14 flows past the horn assembly 22. For example, the horn member of one embodiment has a radius of about 0.875 inches (22.2 mm) and the transverse length of each ring is, as discussed above, about 0.5 inches (12.7 mm). The radius of the inner surface of the column sidewall is approximately 1.75 inches (44.5 mm) so that the transverse spacing between each ring and the inner surface of the column sidewall is about 0.375 inches (9.5 mm). It is contemplated that the spacing between the horn member outer surface and the inner surface of the chamber column sidewall and/or between the agitating members and the inner surface of the chamber column sidewall may be greater or less than described above without departing from the scope of this disclosure.

In general, the horn member may be constructed of a metal having suitable acoustical and mechanical properties. Suitable metals include aluminum, monel, titanium, and some alloy steels. In one preferred embodiment, the metal can be titanium-based material, such as commercially pure titanium, or a titanium alloy (e.g., $Ti_6Al_4V$). It is also contemplated that all or part of the horn member may be coated with another metal. In one particularly suitable embodiment, the agitating members are constructed of the same material as the horn member, and are more suitably formed integrally with the horn member. In other embodiments, one or more of the agitating members may instead be formed integrally with the horn member. In other embodiments, one or more of the agitating members may instead be formed separate from the horn member and connected thereto to form the horn assembly.

In one embodiment, a baffle assemble (not shown) can be disposed within the interior space of the chamber column, and in particular generally transversely adjacent the inner surface of the sidewall and in generally transversely opposed relationship with the horn assembly. The baffle assemble comprises one or more baffle members disposed adjacent the inner surface of the column sidewall and extending at least in part transversely inward from the inner surface of the sidewall toward the horn assembly. The baffle members can facilitate the flow of effluent over the agitating members of the horn assembly. A suitable baffle assemble is described more fully in co-pending application, Reference No. K-C 64122562 (KCC 5091), which is hereby incorporated by reference to the extent it is consistent herewith.

To begin the adsorption process in the ultrasonic treatment chamber, one or more desired functional compounds (not shown) are added to a stir tank 27 and dissolved in an aqueous solution with stirring at a speed of from about 50 rpm to about 800 rpm. Suitably, the aqueous solution contains from about 0.1% (by weight solution) to about 50% (by weight solution) functional compounds. The aqueous solution typically is at a temperature of from about 20° C. to about 90° C. and a pH of from about 2.0 to about 10. Referring to FIG. 1, once dissolved, the fluid 60 is introduced through the inlet end 30 of the ultrasonic treatment chamber 10 of the ultrasonic treatment system 200. The aqueous solution containing the functional compounds is introduced into the ultrasonic treatment chamber at a flow rate of from about 100 milliliters/minute to about 20 liters/minute. More suitably, the aqueous solution is introduced into the ultrasonic treatment chamber at a flow rate of from about 0.5 liters/minute to about 6 liters/minute.

Typically, the ultrasonic treatment system 200 uses a pump 62 to pump the fluid 60 from the stir tank 27 to the inlet end 30 of the ultrasonic treatment chamber 10 of the ultrasonic treatment system 200. Suitable pumps for use in pumping the aqueous solution from the stir tank to the inlet end of the ultrasonic treatment chamber can include, for example, diaphragm pumps, peristaltic pumps, centrifugal pumps, and magnetically coupled gear pumps. In one particularly preferred embodiment, the pump is a magnetically coupled gear pump, manufactured by Micropump Corporation (Vancouver, Wash.), operating at a fluid flow rate of from about 0.1 liters/minute to about 6.0 liters/minute.

In one embodiment, the ultrasonic treatment system 200 comprises a flow control valve 122 as shown in FIG. 1. The flow control valve 122 suitably is a needle valve or ball valve and is used to regulate the flow rate of the fluid (e.g., aqueous solution containing functional compounds) pumped using pump 62 into the ultrasonic treatment chamber 10. Particularly, the flow control valve is advantageous if the pump discharge flow rate is greater than the desired flow rate into the chamber. Suitable flow control valves are commercially available from Parker (Cleveland, Ohio).

In another embodiment, the ultrasonic treatment system can comprise one or more pressure gauges. For example, in FIG. 1, pressure gauges 124 and 126 are used in the ultrasonic treatment system 200. The pressure gauges can be used to monitor the pressure drop across the strainer units described more fully below. Suitable pressure gauges are commercially available from Ashcroft (Stratford, Conn.).

Additionally, the fluid can be run through one or more strainer units disposed along the flow path of the stirred solution from the pump to the inlet of the chamber to filter out particulate material from the solution before it reaches the chamber. For example, as shown in FIG. 1, the solution 60 is run through a first strainer unit 80, constructed to filter out particles sized from about 30 microns to about 50 microns, more suitably about 40 microns, followed by a second strainer unit 82 downstream from the first strainer unit 80 constructed to filter out particles sized from about 5 microns to about 20 microns, more suitably about 15 microns. It is understood, however, that only one, or more than two strainer units may be used, or that the strainer units may be omitted altogether, without departing from the scope of this disclosure.

Once the fluid is introduced into the ultrasonic treatment chamber of the ultrasonic treatment system, the fluid is contacted with the energized adsorbent. Specifically, as the fluid flows through the ultrasonic treatment system, the functional compounds in the fluid are adsorbed to the surface of the energized adsorbent. The fluid is typically contacted with the energized adsorbent for a time period of from about 10 seconds to about 10 minutes, more suitably, from about 5 minutes to about 10 minutes.

After the compounds have been adsorbed to the energized adsorbent 100, the fluid 90, containing the produced carrier component, exits the ultrasonic treatment chamber 10 through an outlet end 38. The outlet end 38 is capable of letting the fluid 90 escape from the chamber 10, while providing enough flow resistance to keep the pressure within the chamber 10 at a suitable level. Typically, the pressure within the chamber 10 is maintained within a range of from about 1 pound/square inch (psi) to about 10 psi.

Once the carrier component of the delivery system is produced, the carrier component is contacted with a substrate. In one embodiment, examples of substrates that will benefit from the functional compounds delivered by the delivery system include substrates such as woven and non-woven materials made from a polyolefin polymer such as polypropylene, polyethylene, polyester, and the like. These substrates are then used in products such as child care articles, face mask fabrics, air filtration fabrics, medical gowns, medical drapes, wipes, hand towels, facial tissue, bath tissue, transdermal delivery devices, wound dressings, automobile covers, boat covers, and deck furniture.

Although not needed, in some embodiments, it may be desirable to pre-treat or post-treat the polymeric substrates which may further serve to affix the carrier component of the delivery system to the materials. For example, substrates made from synthetic polymers can undergo a pretreatment process for increasing the negative surface charge. In one embodiment, such pretreatment processes include subjecting the substrate to a corona treatment or to an electret treatment. An electret treatment, for example, is disclosed in U.S. Pat. No. 5,964,926 issued to Cohen, which is incorporated herein by reference in its entirety. Such pretreatments have been found not only to increase the negative surface charge of polymeric materials, but also assist in wetting out the polymer and enhancing surface adhesion between the polymer and the carrier component of the delivery system of the present disclosure.

In addition to pretreatment processes, substrates contacted with the carrier components can also undergo various post treatment processes which further serve to affix the components to the substrate. For example, once the carrier component has been contacted with the substrates, the substrates can be subjected to radio frequency radiation or to microwave radiation. Adsorbents, such as alumina, are known to adsorb radio frequency and microwave radiation causing the carrier components to heat. Once heated, it is believed that the components become further embedded into the polymeric substrate. Further, the particles can be heated without also heating the substrate to higher than desired temperatures.

In another embodiment, the substrate is the skin of a patient. Specifically, the carrier component can be combined with a lotion or formulation for transdermal use. For example, the carrier component can contain a UV absorber and be combined with a skin care formulation to be used as a sunscreen lotion or sunblock.

In yet another embodiment, the substrate is tissue inside of the body of a patient, such as an organ or muscle. In such embodiments, the carrier component can be administered to the patient orally, parenterally, intraperitoneally, intravenously, or intradermally. In one particular embodiment, the carrier component of the delivery system can be used with capsules, tablets, pills, powders, and granules for oral administration. In such solid dosage forms, the carrier components are ordinarily combined with one or more adjuvants appropriate to the indicated route of administration. If administered in capsules or tablets, the carrier components can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and or polyvinyl alcohol, and then tableted or encapsulated for convenient administration. Such capsules or tablets can contain a controlled-release formulation such as can be provided in a dispersion of the carrier component in hydroxypropylmethyl cellulose. In the case of capsules, tablets, and pills, the delivery systems can also comprise buffering agents such as sodium citrate, or magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such delivery systems can also comprise adjuvants, such as wetting agents, emulsifying and suspending agents, and sweetening, flavoring, and perfuming agents.

In another embodiment, the delivery systems containing the carrier components can be injected into the patient for the purpose of delivering the functional compounds. Depending upon the carrier component used, the component can be contacted with the patient parenterally, intraperitoneally, intratumor, or intrapleural. The term parental as used herein includes subcutaneous, intravenous, intramuscular, or intrasternal injection, or infusion technique.

Injectable delivery system preparations, for example sterile injectable aqueous or oleaginous suspensions, can be formulated according to the known art using suitable dispersing or wetting agents and suspending agents. Among the acceptable vehicles that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can also be used. Mixtures of solvents and wetting agents discussed herein are also useful.

In one specific injectable embodiment, the delivery system is administered parentally. Formulations for parenteral administration can be in the form of aqueous or non-aqueous isotonic sterile injection solutions or suspensions. These solutions and suspensions can be prepared from sterile powders or granules having one or more of the diluents mentioned for the use in the formulations for oral administration. The carrier components can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Additionally, as noted above, the bound functional compound in the delivery system can be used with or without a triggerable release. In one embodiment, the functional compounds can be selectively released by an environmentally created pH trigger, such as by either a basic or acidic environmental condition. For example, the functional compound can be an antifungal compound that is released in the basic/alkaline environment of a vagina with a yeast infection. In another example, the functional compound is an anti-microbial to treat an infection in the basic environment of the small intestine after it has passed through the acidic environment of the stomach.

Other triggering mechanisms can suitably include exposure to changes in temperature, moisture, chemical stimuli, body exudates, and combinations thereof.

In view of the above, it will be seen that the several objects of the disclosure are achieved and other advantageous results obtained.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the disclosure, it is intended that all matter contained in the above description and shown in the accompanying drawings shall be interpreted as illustrative and not in a limiting sense.

What is claimed is:

1. A process of delivering functional compounds to a substrate, the process comprising:
    energizing an adsorbent with ultrasonic energy using an ultrasonic treatment system comprising an inlet end, an outlet end, and an ultrasonic waveguide assembly, wherein the ultrasonic waveguide assembly is a horn assembly comprising a horn member comprising two or more agitating members connected to the horn member and extending at least in part transversely outward from the outer surface of the horn member in longitudinally spaced relationship with each other, the agitating members and the horn member being constructed and arranged for dynamic motion of the agitating members relative to the horn member upon ultrasonic vibration of the horn member such to create a nodal region of the horn member; wherein the adsorbent is selected from the group consisting of alumina, silica, activated carbon, zeolites and combinations thereof;
    wherein the ultrasonic energy is produced by the ultrasonic waveguide assembly that is ultrasonically excited at a frequency of from about 15,000 Hz to about 100,000 Hz;
    introducing a fluid comprising at least one functional compound through the inlet end at a flow rate of from about 100 ml/min to about 20 L/min; wherein the at least one functional compound is selected from the group consisting of pharmaceuticals, xenobiotics, therapeutic agents, nutritional agents, anti-viral agents, anti-microbial agents, UV absorbers, signal agents, and combinations thereof; wherein the fluid is at a temperature of from about 20° C. to about 90° C. and has a pH of from about 2.0 to about 10.0;
    adsorbing the at least one functional compound to the surface of the energized adsorbent to form a carrier component of a delivery system, wherein the adsorbing step is conducted for a period of from about 10 seconds to about 10 minutes;

removing the carrier component through the outlet end; wherein the pressure within the ultrasonic treatment system is from about 1 psi to about 10 psi; and contacting the carrier component with a substrate; wherein the substrate is selected from the group consisting of a product comprising a polyolefin polymer, the skin of a human or animal, and tissue inside a body of a human or animal.

2. The process as set forth in claim 1 wherein the adsorbent is alumina, the alumina being in the form of a particle selected from the group consisting of alumina particles and alumina covered particles.

3. The process as set forth in claim 2 wherein the particles have a particle size of from about 5 nanometers to less than 500 microns.

4. The process as set forth in claim 1 wherein the ultrasonic energy is produced by the ultrasonic waveguide assembly that is ultrasonically excited at a frequency of from about 20,000 Hz to about 40,000 Hz.

5. The process as set forth in claim 1 wherein the horn member is an elongated cylindrical horn member.

6. The process as set forth in claim 1 wherein the ultrasonic treatment system is a continuous ultrasonic treatment system.

7. The process as set forth in claim 6 wherein the ultrasonic treatment system further comprises an ultrasonic treatment chamber enclosing the horn member.

8. The process as set forth in claim 1 wherein the adsorbing step takes place in a batch process.

9. The process as set forth in claim 1 wherein the adsorbing step is conducted for a period of from about 5 minutes to about 10 minutes.

10. The process as set forth in claim 1 wherein the substrate is a woven or non-woven material made from a polyolefin polymer.

11. The process as set forth in claim 10 further comprising pre-treating the substrate prior to contacting the carrier component with the substrate.

12. The process as set forth in claim 10 further comprising post-treating the substrate subsequent to contacting the carrier component with the substrate.

13. The process as set forth in claim 1 wherein the substrate is tissue inside of the body of a patient.

14. The process as set forth in claim 1 wherein the functional compound is selected from the group consisting of pharmaceuticals and signal agents.

15. The process as set forth in claim 1 wherein the functional compound is selected from the group consisting of hydrocortisone, tetracycline, salicylanilide, albofungin, an anthraquinone dye, baicalin hydrate, baicalein, daunorubicin, salicylamide, salacetamide, salsalate, ascorbic acid, aspartame, salicylaldehyde and a UV absorber.

* * * * *